(12) United States Patent
Brooks et al.

(10) Patent No.: US 8,964,936 B2
(45) Date of Patent: *Feb. 24, 2015

(54) DEDICATED BREAST RADIATION IMAGING/THERAPY SYSTEM

(75) Inventors: Kenneth Brooks, Knoxville, TN (US); Jay A. Stein, Boston, MA (US); Andrew P. Smith, Lexington, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/558,146

(22) Filed: Jul. 25, 2012

(65) Prior Publication Data

US 2012/0288057 A1   Nov. 15, 2012

Related U.S. Application Data

(60) Continuation of application No. 13/109,460, filed on May 17, 2011, now Pat. No. 8,254,521, which is a division of application No. 11/944,196, filed on Nov. 21, 2007, now Pat. No. 7,957,508, which is a continuation-in-part of application No. 11/903,859, filed on Sep. 24, 2007, and a continuation-in-part of application No. PCT/US2007/017470, filed on Aug. 3, 2007.

(60) Provisional application No. 60/835,803, filed on Aug. 3, 2006.

(51) Int. Cl.
*A61B 6/03* (2006.01)
*A61B 6/04* (2006.01)
*A61N 5/10* (2006.01)
*A61B 6/00* (2006.01)

(52) U.S. Cl.
CPC .............. *A61N 5/1049* (2013.01); *A61B 6/502* (2013.01); *A61N 5/10* (2013.01); *A61N 5/1081* (2013.01); *A61N 5/1082* (2013.01); *A61B 6/032* (2013.01); *A61B 6/0414* (2013.01); *A61N 2005/1058* (2013.01); *A61N 2005/1061* (2013.01); *A61N 2005/1087* (2013.01); *A61N 2005/1097* (2013.01)
USPC .............................................. 378/37; 378/20

(58) Field of Classification Search
USPC .................................. 378/37, 65, 20; 600/2, 3
See application file for complete search history.

(56) References Cited

U.S. PATENT DOCUMENTS

| | | |
|---|---|---|
| 3,165,630 A | 1/1965 | Bielat et al. |
| 3,556,081 A | 1/1971 | Jones |

(Continued)

FOREIGN PATENT DOCUMENTS

GB         2068700 A        8/1981

OTHER PUBLICATIONS

H.E. Johns & J.R. Cunningham. "The Physics of Radiology", Ch. Thomas, 1983; S.C.

(Continued)

*Primary Examiner* — Allen C. Ho

(57) ABSTRACT

System, apparatus and methods specialized for breast and related tissue radiation therapy and imaging of a prone patient but also usable for supine patient if desired or needed. A special treatment radiation source such as a LINAC unit generates radiation of types and energy ranges specifically matched to breast tissue. Any one or more of several imaging technologies may be used to localize the tissue to be irradiated and to generate information for therapy planning, adjustment, and verification.

4 Claims, 14 Drawing Sheets

(56) References Cited

U.S. PATENT DOCUMENTS

| | | | |
|---|---|---|---|
| 3,578,971 A | 5/1971 | Lasky | |
| 3,852,610 A | 12/1974 | McIntyre | |
| 3,963,933 A | 6/1976 | Henkes, Jr. | |
| 3,973,126 A | 8/1976 | Redington et al. | |
| 4,015,836 A | 4/1977 | Redington et al. | |
| 4,051,380 A | 9/1977 | Lasky | |
| 4,726,046 A | 2/1988 | Nunan | |
| 4,868,843 A | 9/1989 | Nunan | |
| 4,988,919 A | 1/1991 | Tanabe et al. | |
| 4,998,268 A | 3/1991 | Winter | |
| 5,008,907 A | 4/1991 | Norman et al. | |
| 5,078,142 A | 1/1992 | Siczek et al. | |
| 5,422,926 A | 6/1995 | Smith et al. | |
| 5,426,685 A | 6/1995 | Pellegrino et al. | |
| 5,548,627 A | 8/1996 | Swerdloff et al. | |
| 5,564,438 A | 10/1996 | Merchant | |
| 5,574,763 A | 11/1996 | Dehner | |
| 5,583,908 A | 12/1996 | Antich et al. | |
| 5,622,187 A | 4/1997 | Carol | |
| 5,682,890 A | 11/1997 | Kormos et al. | |
| 5,803,912 A | 9/1998 | Siczek et al. | |
| 5,803,913 A | 9/1998 | Khalkhali et al. | |
| 5,851,182 A | 12/1998 | Sahadevan | |
| 6,179,766 B1 | 1/2001 | Dickerson | |
| 6,279,579 B1 | 8/2001 | Riaziat et al. | |
| 6,298,114 B1 | 10/2001 | Yoda | |
| 6,405,072 B1 | 6/2002 | Cosman | |
| 6,463,122 B1 | 10/2002 | Moore | |
| 6,480,565 B1 | 11/2002 | Ning | |
| 6,661,870 B2 | 12/2003 | Kapatoes et al. | |
| 6,662,036 B2 | 12/2003 | Cosman | |
| 6,748,044 B2 | 6/2004 | Sabol et al. | |
| 6,883,194 B2 | 4/2005 | Corbeil et al. | |
| 6,987,831 B2 | 1/2006 | Ning | |
| 7,016,522 B2 | 3/2006 | Bani-Hashemi | |
| 7,046,831 B2 | 5/2006 | Ruchala et al. | |
| 7,122,803 B2 | 10/2006 | Jing et al. | |
| 7,123,684 B2 | 10/2006 | Jing et al. | |
| 7,154,991 B2 | 12/2006 | Earnst et al. | |
| 7,199,382 B2 | 4/2007 | Rigney et al. | |
| 7,204,254 B2 | 4/2007 | Riaziat et al. | |
| 7,233,005 B2 | 6/2007 | Bogdanovich et al. | |
| 7,239,684 B2 | 7/2007 | Hara et al. | |
| 7,245,694 B2 | 7/2007 | Jing et al. | |
| 7,402,822 B2 | 7/2008 | Guertin et al. | |
| 7,450,688 B2 | 11/2008 | Becker et al. | |
| 7,492,858 B2 | 2/2009 | Partain et al. | |
| 7,496,398 B2 | 2/2009 | Nields et al. | |
| 7,519,149 B2 | 4/2009 | Mackie et al. | |
| 7,526,066 B2 | 4/2009 | Koshnitsky et al. | |
| 7,561,661 B2 | 7/2009 | Ullberg et al. | |
| 7,649,981 B2 | 1/2010 | Seppi et al. | |
| 7,668,287 B2 | 2/2010 | Sendai | |
| 7,736,292 B2 * | 6/2010 | Hermann et al. | 600/7 |
| 7,957,503 B2 * | 6/2011 | Kobayashi | 378/37 |
| 2002/0143249 A1 | 10/2002 | Tornai et al. | |
| 2003/0073895 A1 | 4/2003 | Nields et al. | |
| 2004/0171933 A1 | 9/2004 | Stoller et al. | |
| 2006/0239398 A1 | 10/2006 | McCroskey et al. | |
| 2006/0262898 A1 | 11/2006 | Partain et al. | |
| 2006/0293644 A1 | 12/2006 | Umstadter | |
| 2007/0033735 A1 | 2/2007 | Formenti | |
| 2007/0167664 A1 | 7/2007 | Hermann et al. | |
| 2007/0269000 A1 | 11/2007 | Partain et al. | |
| 2008/0043905 A1 * | 2/2008 | Hassanpourgol | 378/37 |
| 2009/0080604 A1 * | 3/2009 | Shores et al. | 378/37 |

OTHER PUBLICATIONS

Jozsef, Gabor et al. "Application of radiosurgery principles to a target in the breast: A dosimetric study", Medical Physics, vol. 27, No. 5, May 2000.

C. Kurtman et al., "Three-Dimensional conformal breast irradiation in the prone position" Brazilian Journal of Medical and Biological Research (2003) 36: 1441-1446.

Formenti, Silvia C. MD. "External-Beam Partial-Breast Irradiation", Seminars in Radiation Oncology 15:92-99, 2005.

Nov. 28, 2008 International search report in connection with corresponding international patent application No. PCT/US2008/077381.

* cited by examiner

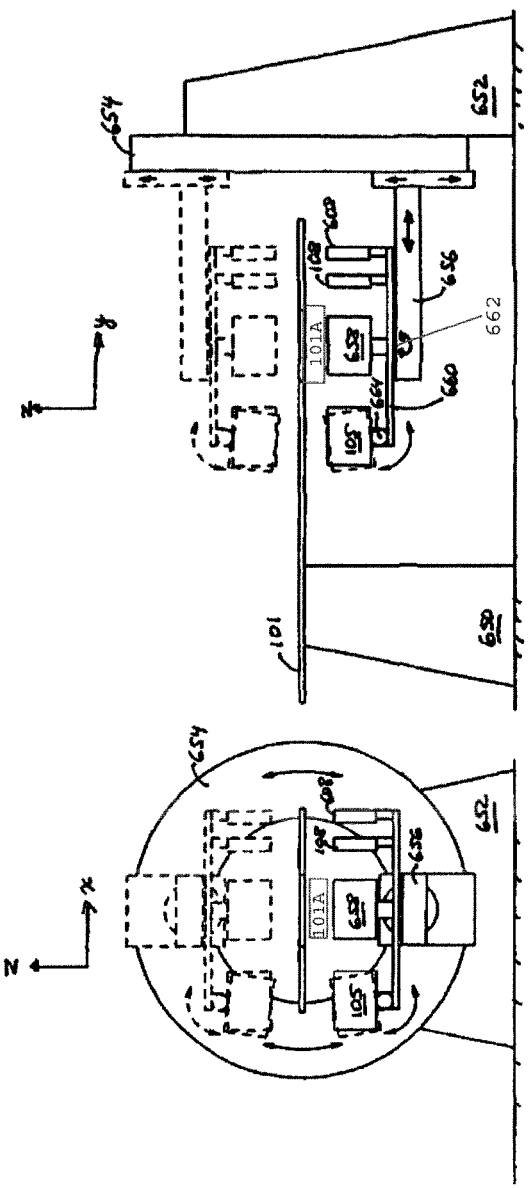

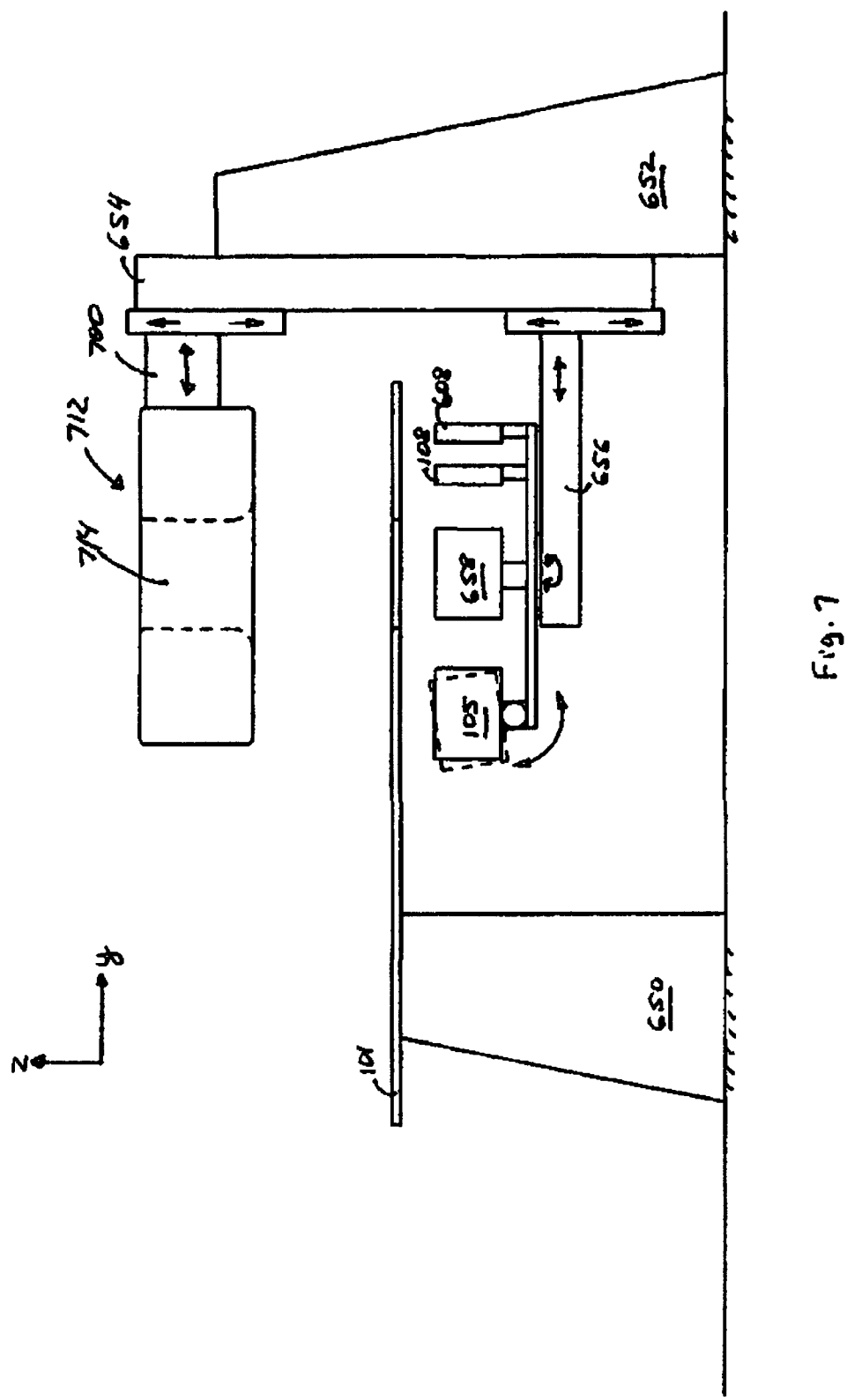

US 8,964,936 B2

DEDICATED BREAST RADIATION IMAGING/THERAPY SYSTEM

REFERENCE TO RELATED APPLICATIONS

This application is a continuation of U.S. application Ser. No. 13/109,460 filed May 17, 2011, now U.S. Pat. No. 8,254,521, issued Aug. 28, 2012, which is a divisional of U.S. application Ser. No. 11/944,196, filed Nov. 21, 2007, now U.S. Pat. No. 7,957,508, issued Jun. 7, 2011, which in turn is a continuation-in-part of U.S. application Ser. No. 11/903,859, filed Sep. 24, 2007, and a continuation-in-part of International application No. PCT/US07/017470 filed, Aug. 3, 2007, claiming the benefit of U.S. Provisional Application No. 60/835,803, filed Aug. 3, 2006. This patent specification incorporates by reference the content of each of said earlier-filed applications, as well as the contents of the references cited in the text below.

FIELD

This patent specification is in the field of radiation therapy and associated imaging and therapy planning/adjustment/verification, and specifically pertains to dedicated, specialized radiation therapy of a patient's breast and associated imaging, planning, and verification procedures.

BACKGROUND

Radiation therapy has long been used in medicine. Typically, high energy radiation from sources such as linear accelerators and radioisotopes is used, especially in whole-body, external beam systems where the radiation may need to penetrate a significant amount of tissue in order to reach the target volume and attain within the target volume the prescribed therapeutic dose level and fractionation scheme. The irradiation of normal tissue is a necessary physical consequence of all modes of radiotherapy and typically becomes the limiting factor in any given patient's therapy regimen. In procedures that use radiation sources inside the patient's body, a similar challenge is the undesirable but unavoidable exposure of normal tissue. Conventional, whole-body, external beam systems can be used for breast therapy as well but their large, whole body geometry tends to lead to undesirable irradiation of significant amounts of healthy tissue. Also, whole body, external beam systems may be designed to irradiate at energy levels that are not optimized for breast tissue. In order to reduce normal tissue irradiation and achieve sufficient target volume dose, efforts have been made to find other approaches for breast radiation therapy, leading to methods that include, in addition to the orthovoltage radiation treatment disclosed in said earlier-filed patent applications, proposals by others such as (1) internal breast brachytherapy which involves inserting catheters or needles in the breast and placing radioactive substances in or through the catheters or needles or using radioactively coated needles, (2) surgically implanting a balloon in the breast and selectively delivering radioactive material to the balloon through a catheter, (3) surgically positioning a miniature x-ray tube inside the breast, (4) external stereotactic brachytherapy that involves compressing the breast between two sets of conforming channels through which a radioactive substance is placed in close proximity to the breast, (5) using orthovoltage radiation from an external kilovoltage x-ray source that irradiates the breast from the side or possibly through a purposely designed surgical opening in the tissue, (6) using a LINAC radiation source that rotates in a horizontal plane to irradiate a downwardly protruding breast of a patient on a table with an opening for the breast, and imaging the breast with that source or an adjunct source, and (7) combining a radioactive substance with a biologically active material designed to uptake selectively in the breast tissue where it decays and provides a therapeutic dose (such as monoclonal antibodies) or a substance which causes the tumor to be more radiosensitive during the treatment.

An external beam radiation therapy treatment typically involves therapy planning in which the location and perhaps other characteristics of a lesion or other target volume or other tissue to be treated or avoided and monitored are identified by one or more imaging technologies such as ultrasound, X-ray computed tomography, static and dynamic planar imaging, nuclear medicine imaging, and magnetic resonance imaging. Information from these imaging modalities is used in computer processing to develop a treatment plan for the directions, energies, and durations of the therapy radiation beams and the number and frequency of the treatment sessions. In addition, before each radiation therapy session images of the lesion and/or other target volume or other tissue may be taken to check the position of the target volume and other tissue relative to the geometry of the radiation therapy system, and various positioning aids may be used in the therapy system to verify and maintain a desired geometric relationship between the radiation treatment beam(s) and the target tissue and possibly other tissue. Brachytherapy also typically involves similar treatment plan and verification procedures. Typically, the treatment plan and verification imaging is done on equipment physically separate from the radiation treatment equipment. Although care can be taken to preserve the position of the tissue of interest relative to frames of reference that pertain to both the imaging equipment and the treatment equipment, there is a risk that transferring the patient from one piece of equipment to another may disturb that relationship, with the result that the actual radiation treatment may not match the planned treatment.

See, for example, H. E. Johns & J. R. Cunningham. The Physics of Radiology, Ch. Thomas, 1983; S. C. Formenti, External-Beam Partial-Breast Irradiation, Seminars in Radiation Oncology, Elsevier 2005, 82-99; G. Jozsef, G. Luxton, S. C. Formenti, Application of radiosurgery principles to a target in the breast, A dosimetric study, Med. Phys. 27 (5). May 2000, 1005-1010; O. Gayou, D. S. Parda, M. Miften, Patient dose and image quality from mega-voltage cone beam computed tomography imaging, Med. Phys. 34 (2). February 2007, 499-506.

Despite such advances in radiation therapy systems, including for breast radiation, it is still desirable to improve breast radiation therapy by making it more effective and efficient.

SUMMARY OF THE DISCLOSURE

Disclosed is a dedicated system for radiotherapy of the breast and related tissue of a patient in the prone position, with radiation beams that can rotate below the patient about a vertical axis but in addition can rotate about an axis angled to the vertical to treat breast-related tissue such as axillary lymph nodes without turning the patient over. Maintaining the patient in the same prone, breast-pendulous position can ensure good registration between the treatment beams and target volume, and good consistency with treatment plans for both breast and related tissue, especially when the patient preferably is maintained in the same position and in the same equipment for treatment planning and/or verification imaging as well as for radiation treatment. Further, the system can include a mode in which the patient can be treated in the supine position or in another position, if desired or if called for by special circumstances. The system includes imaging functionalities that share a spatial frame of reference with the treatment functionalities, whether or not they also share components, and can verify and/or adjust a treatment plan or generate a treatment plan through two-dimensional (2D) and/or three-dimensional (3D) imaging/planning. The distance between the radiation source for treatment/imaging and the target volume can be varied if desired so the radiation source can move about the target volume or some other center rather than about a fixed isocenter. This can be done by one or both of source motion and patient table motion. The system can further include sensors/transmitters that can be implanted or otherwise secured in or to the patient, or can be otherwise fixed relative to a system frame of reference, to verify the position of a target volume or other tissue relative to the radiation beam(s) and/or to measure the radiation dose in two or three dimensions. The sensors/transmitters preferably include data storage and/or transmission functionalities to provide information to the system, preferably on an essentially real time basis subject to inherent information processing and equipment response time delays. As an alternative or addition to being imaged for treatment planning and/or verification in the same set of equipment, the patient can be on a patient table or couch that fits both the treatment/imaging system and conventional imaging modalities such as CT scanners so that the patient can remain in or conveniently and accurately resume the same position, such as the prone position with a breast protruding downwardly through an opening or into a depression of the patient table or couch, when imaged for treatment planning at one system and then when positioned for treatment/verification at another system. The patient can be positioned on the table and couch in the prone position with the protruding breast immobilized in an effort to maintain or accurately resume its position relative to the table or couch, and can be imaged in a CT scanner for radiation planning and then later positioned at the disclosed system for treatment in which the position of the breast or other target tissue relative to the system frame of reference is known from the information provided from treatment planning and the fact that the position of the table or couch relative to the treatment system also is known, e.g., from mechanical, electromagnetic (e.g., optical or electrical) or other table mounting interlocks. The imaging functionalities of the disclosed system can include 2D and/or 3D imaging systems such as portal imaging using the treatment radiation source, an x-ray imaging system using components mounted in known relationship to the system spatial frame of reference, nuclear medicine imaging (including metabolic activity imaging) using detectors also mounted in the same system as the radiation treatment source and in a known spatial relationship with the system frame of reference, ultrasound imaging with transducers maintained in known positions in the system frame of reference, and/or other imaging modalities. Suction or other devices can be used to pull breast tissue away from the chest wall as needed and/or to stabilize the breast for imaging/treatment. The system can be used for traditional treatment plans that use fractional doses over a longer period of time such as a number of weeks or for partial breast irradiation that typically treats only a part of the breast (e.g., a lumpectomy site) but over a shorter period of time such as once or twice a day for five days. Also disclosed are methods of using the system and methods of imaging, treatment planning/verification/adjustment and radiation treatment.

In one non-limiting embodiment the system comprises a table or couch for the patient to lie prone with at least one breast protruding downwardly through an opening or extending into a depression in the table or couch. Preferably a positioning device is used to maintain a reasonably consistent and stable position of the breast relative to the patient table or couch and the imaging and treatment system spatial frame of reference and, if desired, to help pull tissue away from the chest wall. In an imaging mode, the system provides information for identifying the position of the breast, the target volume in the breast and/or of some other tissue relative to both the system geometry and pre-treatment patient geometry by utilizing imaging technologies such as one or more of x-ray planar and computed tomography or tomosynthesis, nuclear medicine, ultrasound, other imaging modalities, and position-indicating and/or monitoring devices that can be implanted in or otherwise secured to or near the tissue of interest and are specifically designed to work within the confines of the system and patient geometry (and preferably can store and/or transmit information regarding position and dose). This pre-treatment imaging takes place before at least the first treatment session but may be repeated before additional treatment sessions, and can also be used to identify or estimate other characteristics such as shape and size of a lesion or other target volume parameters related to the tissue along intended therapy radiation paths and also to identify critical structure volumes whose unintended irradiation is to be minimized, characteristics of other portions of the breast and perhaps of other anatomy, and the like.

In a treatment planning/adjustment/verification mode, the system uses information obtained from other imaging modalities and/or information from the imaging mode of the system disclosed in this patent specification to plan treatment or at least to verify/adjust treatment plans and/or verify the position of the lesion or other target volume and/or of other body parts relative to system and patient geometry. While typically treatment planning and/or verification take place before and/or after a treatment session, it is also possible in the disclosed system and method to augment such procedures with updating the treatment plan before a given radiation fraction is delivered to the patient, and even during delivery, to achieve effective on-the-fly image guided radiation therapy and/or dynamic adaptive radiation therapy. The treatment radiation can be controlled through controlling one or more of, e.g., the treatment beam intensity, duration, and shape on the fly, using feedback from imaging modalities such as portal imaging, ultrasound or another modality, of source within the response delays inherent in the imaging, feedback and radiation beam shaping equipment. In a radiation therapy mode of the system disclosed in this patent specification, a therapy radiation source below the patient table or couch moves about the downwardly extending breast of a patient in the prone position and emits radiation in energy ranges that are uniquely suited to breast-related radiation treatment. Importantly, the therapy radiation source can move not only in a horizontal plane (e.g., about a vertical axis) but also in other planes (e.g., about a non-vertical axis) to irradiate breast-related tissue such as the patient's axilla, target volumes that are very close to the chest wall, and other lymph nodes away from the breast. Also importantly, the therapy radiation source can rotate or otherwise move about the lesion or other target volume or about other loci to direct radiation along paths that maintain a low skin dose or otherwise reduce dose outside the target tissue. The system directs and otherwise controls the radiation, preferably in accordance with current or updated treatment plans.

Preferably, the therapy radiation source is a special linear accelerator (Linac) that has two important characteristics—it emits treatment radiation that can be uniquely suited to breast-related tissue, and it is sufficiently compact to be mounted below the prone patient table for movement about a patient's breast such as in a horizontal plane and also for movement about the breast such as in a plane at an angle to the horizontal in order to direct primary radiation at other target tissue that may be associated with the breast. Thus, the source can rotate about a vertical axis and/or about an axis that extends upwardly but at an angle to the vertical to enable therapy radiation to be directed to target volumes outside the prone patient's breast if desired, such as at or near the patient's chest wall or the patient's axilla. In addition, if desired the therapy radiation source can be moved above the patient or to other positions suitable for irradiation of a supine patient or a patient in another position. The linear accelerator produces a maximum energy that can be set at a value, or can vary, in the range of about 1-10 MeV Bremstrahlung photons, and preferably about 4-6 MeV Bremstrahlung photons. As an alternative example, the treatment radiation can be charged particles including but not limited to particles such as electrons, protons, and deuterons. Electrons for a treatment beam can come from the linear accelerator source when the conventional Bremstrahlung target is removed and appropriate beam shaping fields are provided. Other particles for a treatment beam can come from other accelerating sources known in high-energy physics.

The imaging system preferably uses penetrating radiation from an external source but may use, instead or in addition, radiation emitted from the breast and/or related tissue, such as from a radiation emitting substance injected or otherwise introduced into the patient's body, and can use ultrasound imaging. In one example, portal imaging is used in which a Linac-based source also provides imaging radiation, and an imaging detector that is suitable for such high-energy radiation generates the image(s). Different energy levels of penetrating radiation from the source may be used for imaging versus therapy, if desired. Alternatively, a source different from that used for therapy can be used to provide imaging radiation. As a non-limiting example, imaging radiation can come from an x-ray source of the type typically used in x-ray mammography or for imaging the chest, and the imaging detector can also be of the type used in x-ray mammography or chest radiography, and preferably is a flat panel detector of the type commercially available from the common assignee, Hologic, Inc. If the source of the imaging radiation is internal, suitable imaging detectors are used, such as SPECT, PET, or nuclear medicine imaging detectors. Another imaging modality that can be used is ultrasound, preferably carried out in a manner that also provides information to positionally relate the imaged tissue with the geometry of the therapy radiation system and the patient's reference frame established before therapy and updated as needed during the course of therapy. A CT scanner suitable for breast imaging may be included in the system. Only one of the imaging modalities identified above may be used, or a combination of two or more imaging modalities can be used, to provide information for therapy planning, updating, and verification. Preferably, the imaging system also moves, e.g., rotates, under the prone patient's table, about a vertical or non-vertical axis, and can be moved to the patient level or above the patient if desired to image a patient who is in the prone or other position, and preferably but not necessarily the rotation or other motion centers on the lesion or other target volume. Preferably, the imaging modality produces three-dimensional information, such as information based on tomosynthesis, CT scanning, stereotactic imaging, 3D ultrasound imaging, or other 3D imaging modalities.

The imaging information is used to generate both traditional, static, forward planned treatment plans as well as inverse planned, dynamic intensity modulated treatment plans using state-of-the-art integrated optimization methods that can be based on known treatment planning technology used for whole-body radiation therapy systems, such as those commercially available from Varian Medical Systems of Palo Alto, Calif., Philips Medical Systems of Andover, Mass., and CMS Inc. of St. Louis, Mo., but taking into account the unique geometry of the breast therapy/imaging system disclosed in this patent specification and its other unique parameters such as optimized multileaf collimator leaf sizes designed for targeting smaller breast lesions or other breast-related target volumes rather than the typically larger target volumes addressed by whole body systems, and the photon or particle energy levels which are also closely matched to breast-related tissue.

The patient's breast can be immobilized and maintained in position for pre-treatment planning in one or more imaging system and for treatment by devices that include but are not limited to thermoplastics, vacuum fixation bags, foam padding, appendage fixation devices, cones, vacuum and/or adhesives applied to such cones, or other means. Devices of this nature are proposed, e.g., by MedTec of Orange City, Iowa under the trade name Horizon Breastboard and by Varian Medical Systems.

BRIEF DESCRIPTION OF THE DRAWINGS

The features of the subject matter of this disclosure can be more readily understood from the following detailed description with reference to the accompanying drawings wherein:

FIG. 6a is a schematic illustration of an example of a radiation therapy and imaging system in side view, and FIG. 6b is a schematic illustration of the system in a front view.

FIG. 7 is a schematic illustration of a system in side view that includes CT imaging provisions.

DETAILED DESCRIPTION

In describing preferred embodiments, specific terminology is employed for the sake of clarity. However, the disclosure of this patent specification is not intended to be limited to the specific terminology so selected and it is to be understood that each specific element includes all technical equivalents that operate in a similar manner. In addition, a detailed description of known functions and configurations will be omitted when it may obscure the subject matter of the present invention.

Figure 1:
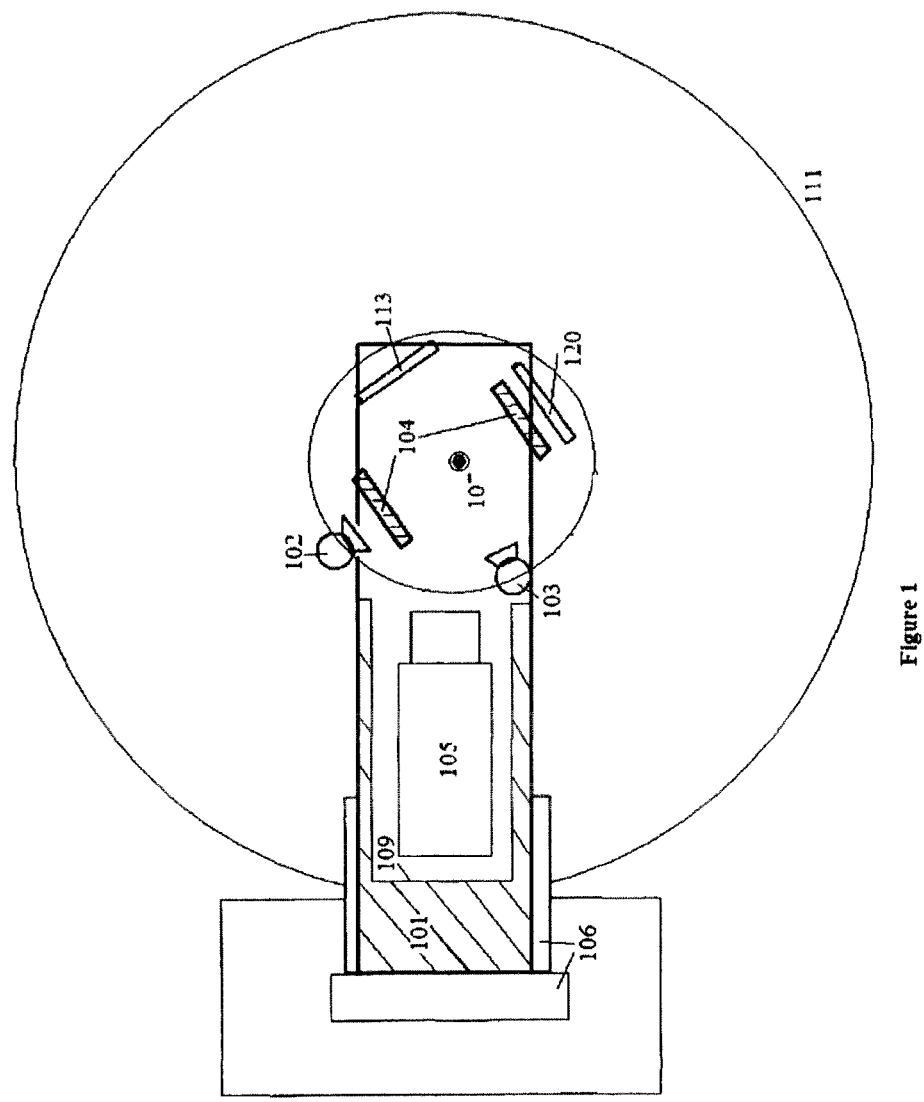
FIG. 1 illustrates a top view of an embodiment comprising an integration of a breast therapy system and multiple breast imaging systems.

As illustrated in FIG. 1, a non-limiting example of the system comprises a table or couch 101 that is especially adapted to support a patient in the prone position but may also be used to support a patient in other positions such as in the supine position or another position. FIG. 1 also illustrates one or more imaging systems discussed below in more detail for localizing and identifying a lesion or abnormality or target volume, a radiation source such as a special Linear Accelerator (LINAC) 105 for producing therapy radiation, and a motorized cantilevered stand 106. For clarity, the table is illustrated in FIG. 1 with a cutout 109 to allow visualizing the components that are below the table. Preferably the LINAC device 105 is a compact version capable of producing penetrating radiation uniquely suited to breast-related tissue rather than optimized for whole-body radiation therapy. Preferably, the imaging and therapy systems move about the patient's breast, preferably though not necessarily in rotation, and preferably the motion is centered on the lesion or target volume for therapy irradiation. However, as discussed below the system may include provisions for moving the therapy and/or imaging components in a manner suitable for patients in other patient positions, such as the supine patient position.

The imaging systems in FIG. 1 example may include: an x-ray system that uses an x-ray source 102 and x-ray digital imaging detector (flat panel) 120, a stereotactic x-ray imaging system where two x-ray sources 102 and 103 are used with respective x-ray imaging panels 120 and 113 (or one set of a source such as 102 and a detector such as 120 is moved to one position for one x-ray image and another position for another image taken at a different angle relative to the patient's breast), PET or SPECT imaging panels or ultrasound transducers 104, combinations of two or more of the imaging systems identified above, or other imaging systems. If an x-ray imaging system is used, it can use only one, or both, of sources 102 and 103 and respective x-ray detector panels 113 and 120, to image the patient's breast or other patient tissue. Imaging source 102 and x-ray panel 120 are mounted to move about the breast as a unit, to image the breast from different angles. If source 103 and panel 113 are used, they also rotate or otherwise move as a unit, and if both source/panel sets are used, the two sets can rotate as a unit or individually. In each case, the motion can be about a center 107 that can be at the lesion or target volume or about some other center. The x-ray imaging system(s) may be used to derive projection tomosynthesis image data, for example by using motion and image reconstruction as disclosed in commonly assigned U.S. Pat. Nos. 7,245,694, 7,233,005, 7,123,684, 7,122,803, 6,851,851, and 6,282,264, or to derive stereotactic information, for example as discussed in U.S. Pat. No. 5,803,912 or U.S. Patent Publication 2004/0171933 A1.

FIGS. 2a-2d are top views of the system that illustrate examples of the range of positions of the therapy system in relation to patient table 101 (that again is shown with cutout 109 to allow seeing components below the table). A motorized stand 106 supports table 101 for up-down motion and, if desirable, for motion along and across the length of the table, and also can support the imaging and therapy systems for rotation in a circle 111 representing a preferred 360 degree range of rotation of LINAC 105 and of the imaging system(s) around a selected center 107. If portal imaging is used, a portal imaging detector 108 and the LINAC device 105 can move as a unit for imaging.

Figure 2A:
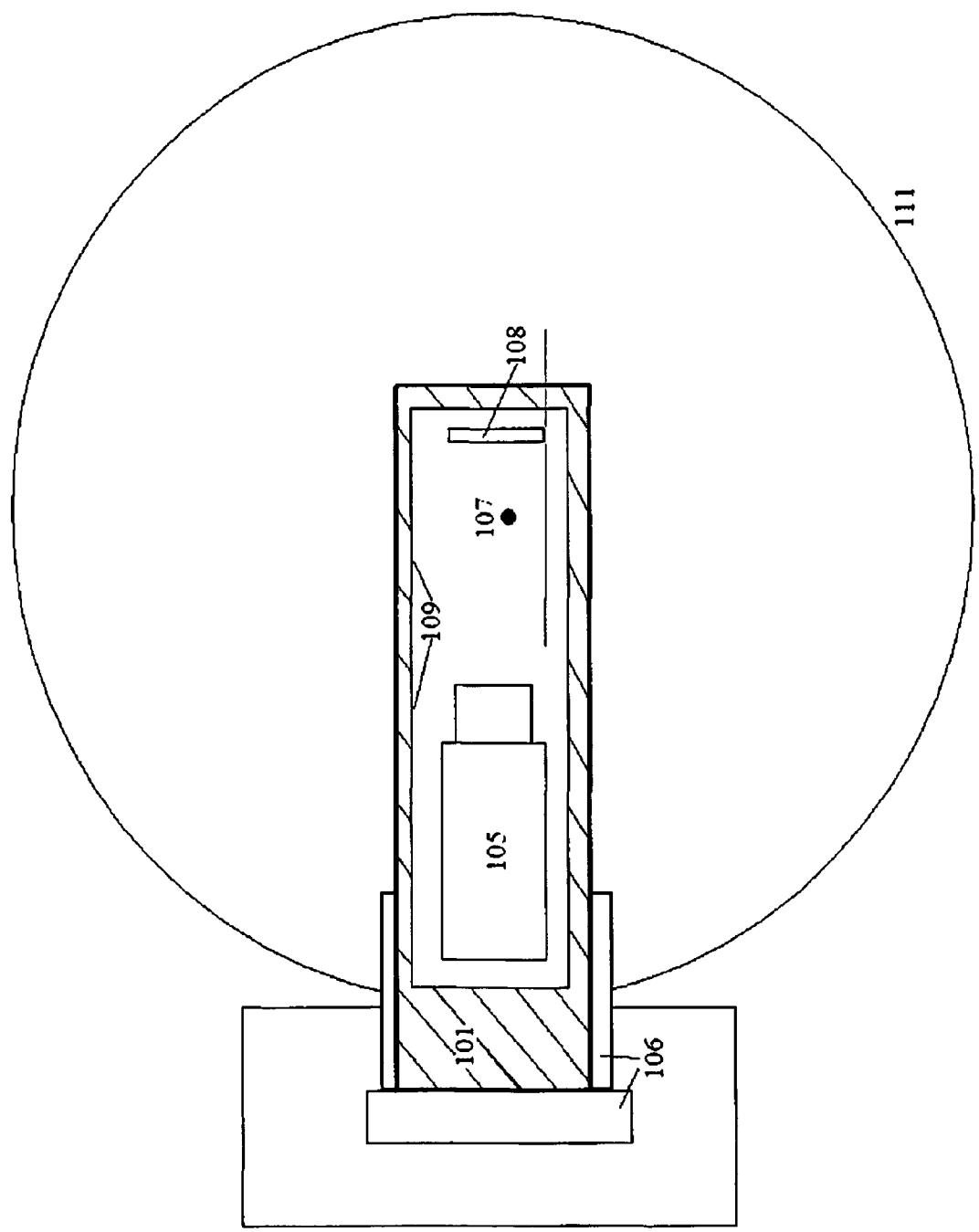
FIGS. 2a-2d illustrate a top view of the therapy system of FIG. 1 in several different positions of a therapy radiation source.
Figure 2B:
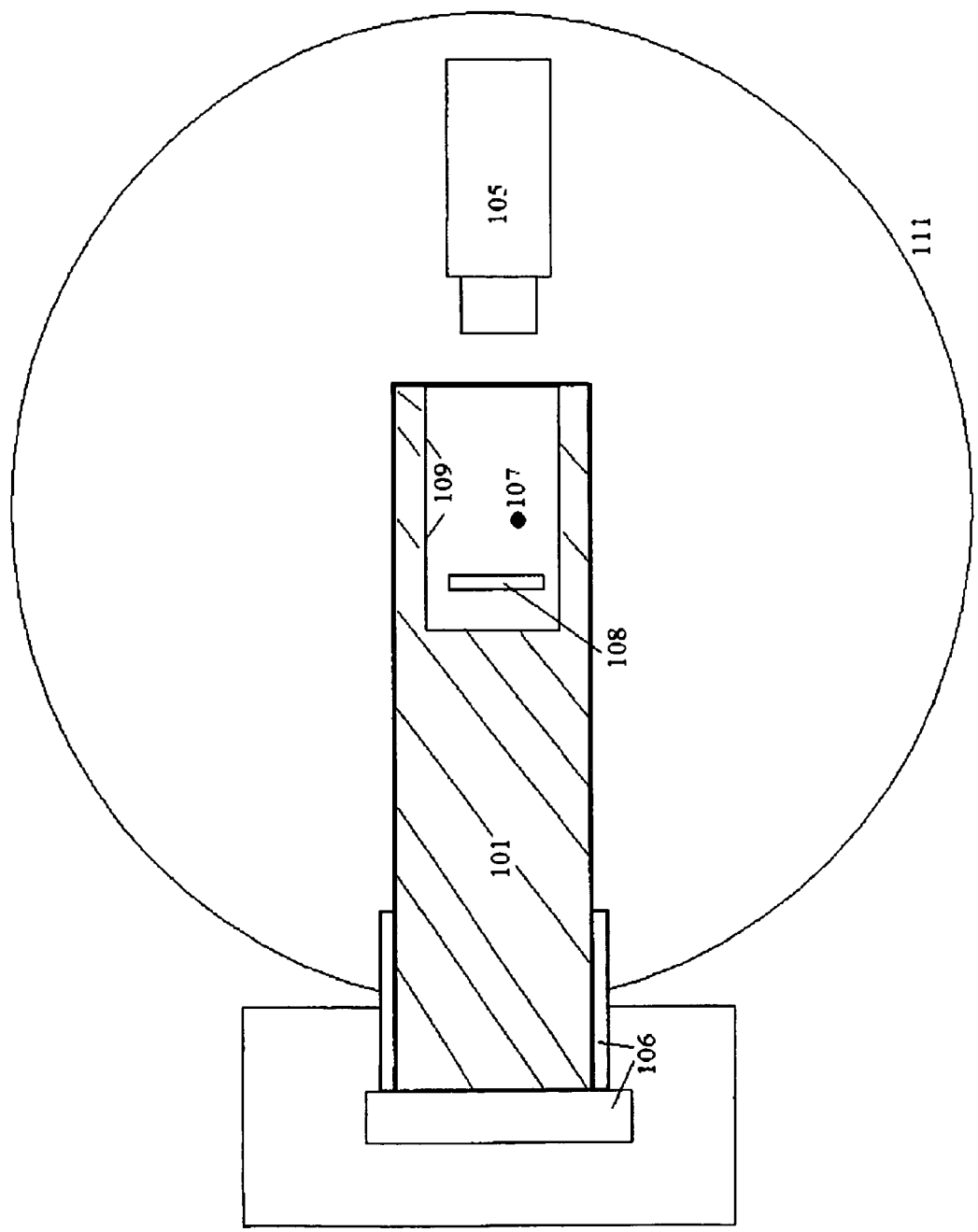
Figure 2C:
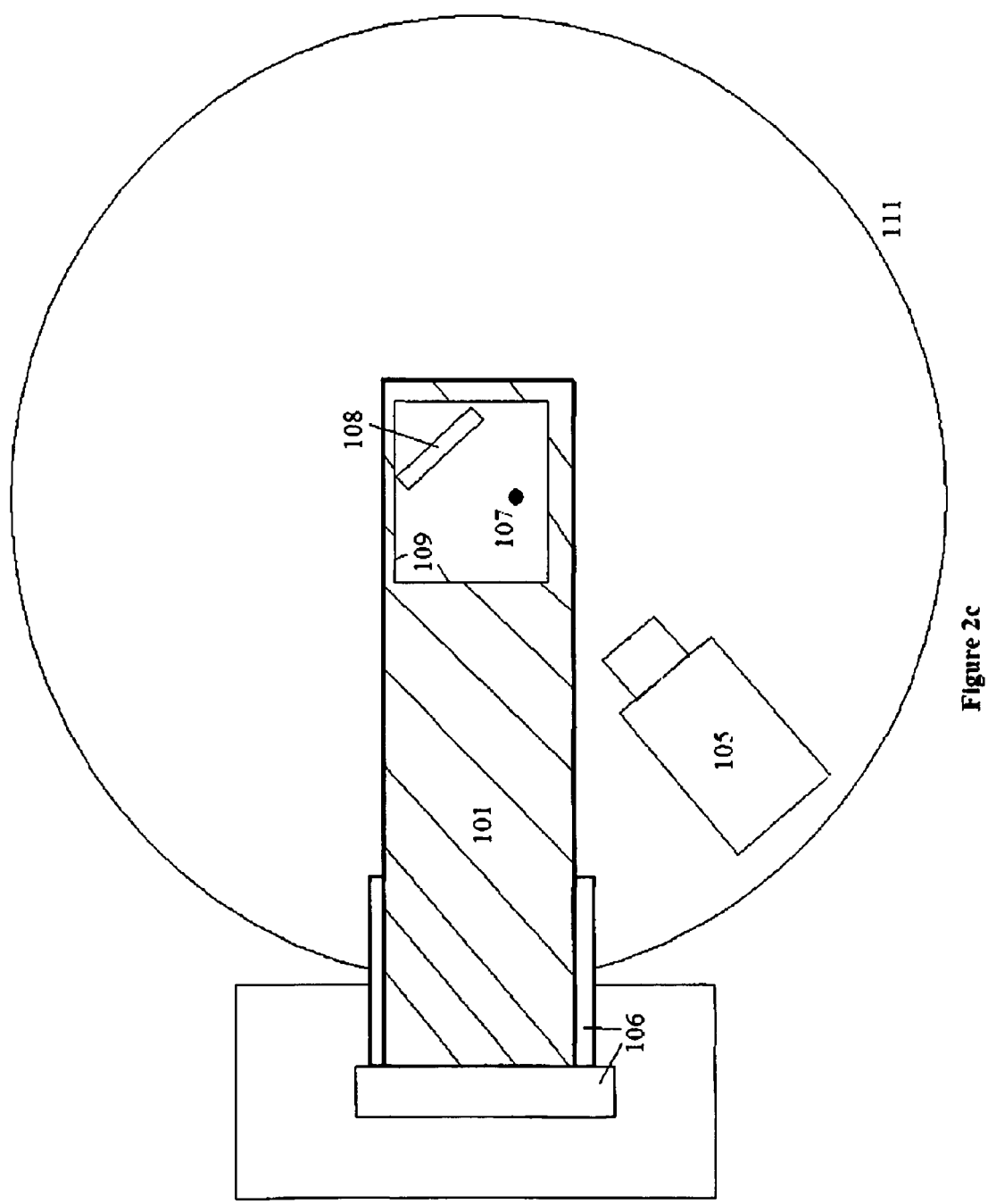
Figure 2D:
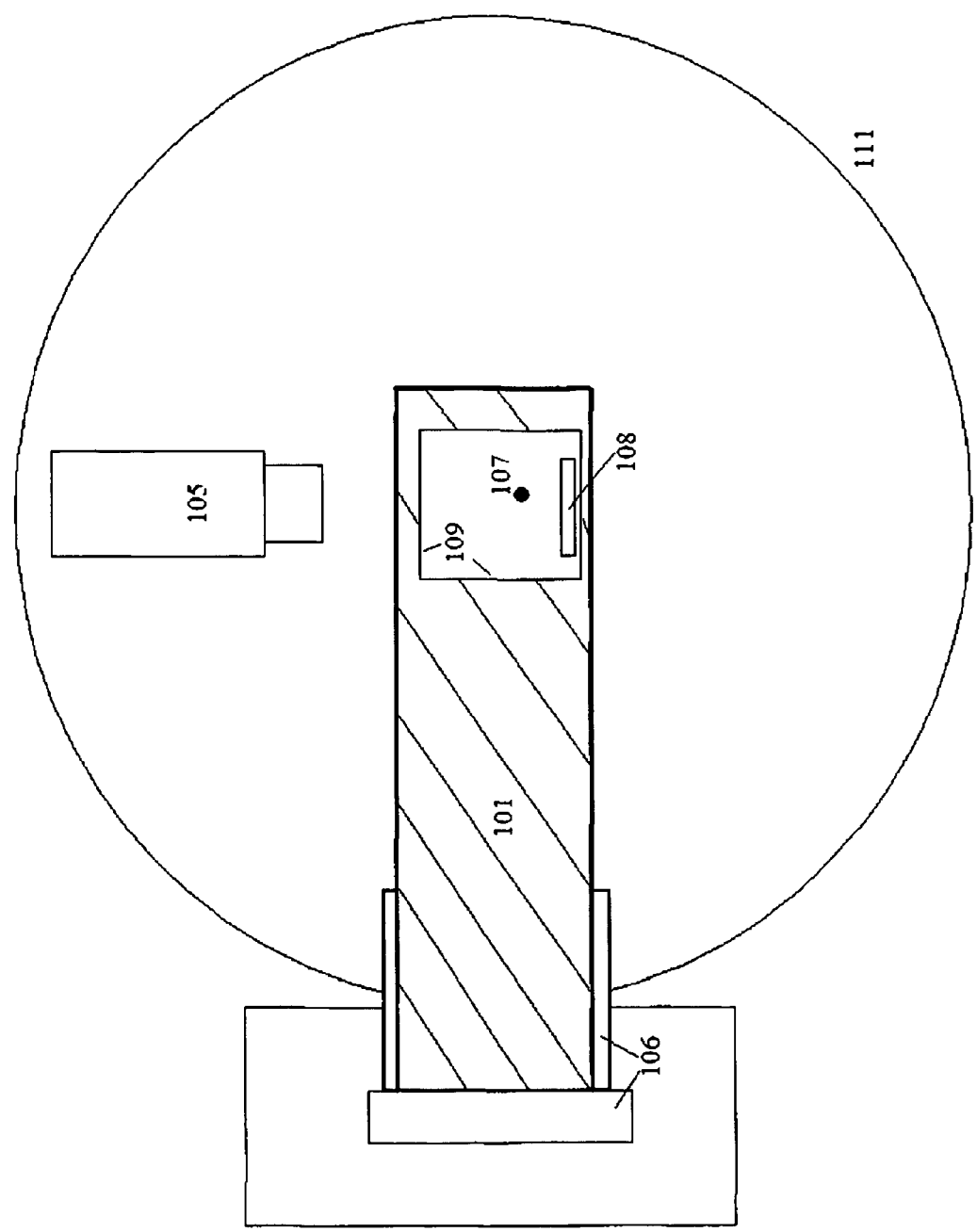

FIG. 2a illustrates the LINAC device at 0° relative to prone table 101 and isocenter 107. Illustrative cutout 109 reveals the LINAC source 105, center 107, and a radiation detector 108. FIG. 2b illustrates LINAC source 105 at 180° relative to patient table 101 and center 107. Illustrative cutout 109 reveals center 107 and detector 108. FIG. 2c illustrates LINAC source 105 at approximately 45° relative to table 101 and center 107. Illustrative cutout 109 reveals center 107 and detector 108. FIG. 2d illustrates LINAC source 105 at 270° relative to prone table 101 and center 107. Illustrative cutout 109 reveals center 107 and detector 108. In a non-limiting example, circle 111 representing the diameter and range of rotation of LINAC source 105 and imaging detector 108 preferably has a diameter of approximately three meters. Stand 106 preferably extends approximately 1 meter from a wall. A range of rotation through an angle smaller than 360° can be used as an alternative.

Figure 3:
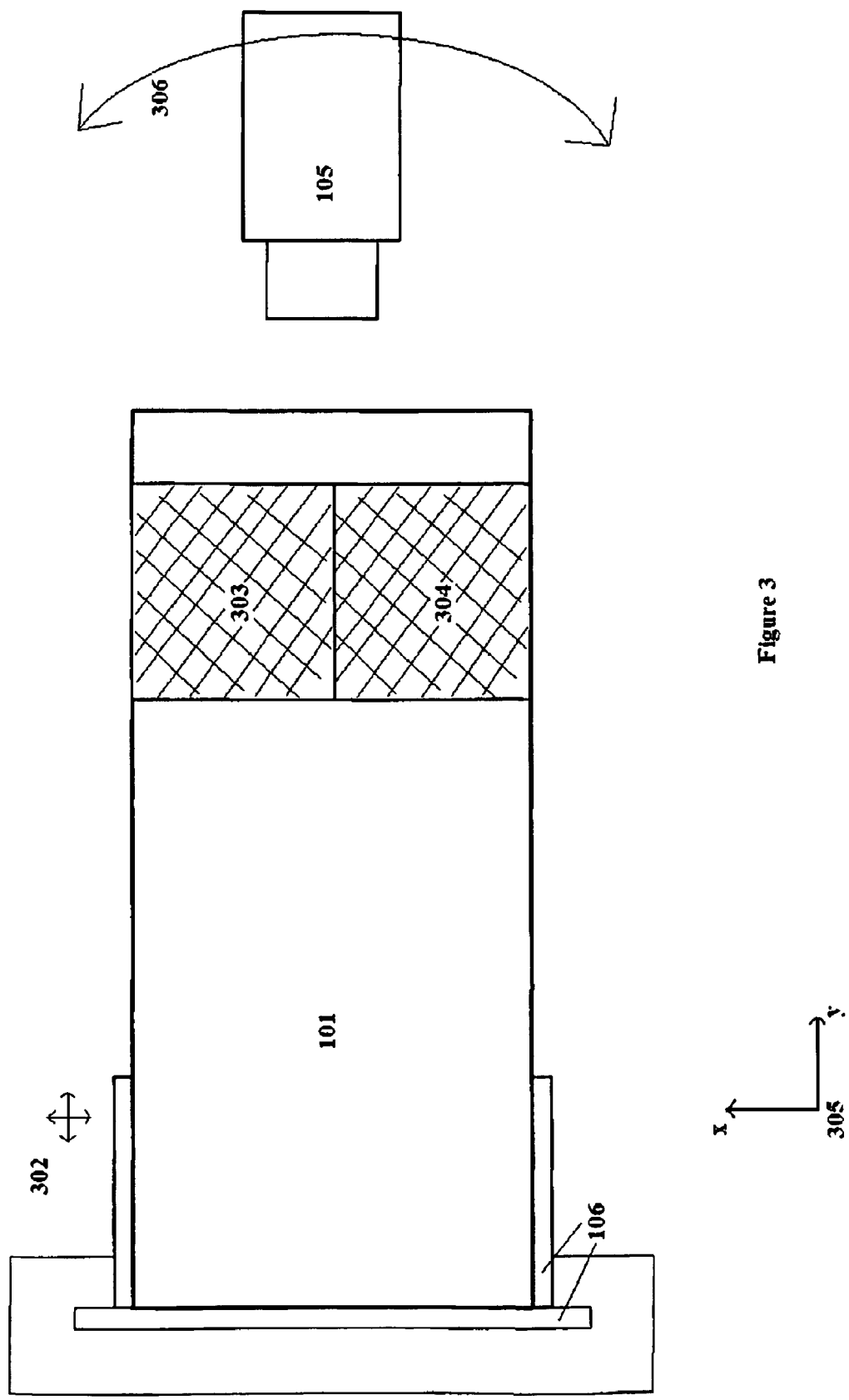
FIG. 3 illustrates a top view of a patient table for use in the system of FIG. 1.

FIG. 3 illustrates additional features of patient table 101 as seen in top plan view. Table 101 comprises left and right removable mesh panels 303, 304 that cover respective left and right openings in the table. When a mesh panel is removed from the table, the opening allows a patient's breast to extend downwardly for imaging and/or radiation therapy. The panels are designed to be replaced by a breast stabilizing aide, 101A (FIGS. 6a and 6b), such as an aide made of an "Aquaplast" material or comparable material forming a semi-rigid thermoplastic surface around a breast. The system operating in an imaging mode with some or all of the associated modalities can be used to help establish the position and orientation of the stabilizing aide and to correlate what will become a semi-rigid surface of the thermoplastic material to the breast, the target volumes and the system reference frames. Additional or alternative stabilizing aides such as other thermoplastics, vacuum fixation, personal positioning cups, or variations of positioning boards and coaches may be employed in the radiotherapy apparatus disclosed herein.

The stabilizing aide(s) or combinations thereof preferably facilitate immobilizing a breast for imaging so that the target volume can be accurately and conveniently located in relation to patient and system geometry and the lesion or other radiation target volume can then be given a planned radiotherapy dosage. The use of stabilizing aides described herein and variations thereof can assist the radiotherapy system in providing consistent and precise irradiation of a patient's anatomy on a daily or other basis. The stabilizing aides described herein are relatively inexpensive and can be re-fabricated as needed during the course of therapy for clinical (anatomy changes, adema, etc) or patient comfort requirements. As in the case of the stereotactic imaging and biopsy table available from the common assignee under the name MultiCare, the table surface can be shaped, originally or with the help of special pillows, to provide patient comfort and to extend the appropriate anatomy as much as possible below the patient table.

Additionally, implantable or otherwise attachable position and/or dose sensors 107a (FIG. 4a) for use within or near a patient's breast or other anatomy can be utilized to further increase the accuracy and effectiveness of an individualized patient radiotherapy treatment plan, optionally in combination with one or more breast stabilizing aides. There are implantable position sensors capable of communicating anatomical positioning information, an example of which is available from CALYPSO Medical ad Seattle, Wash. One or more implantable position sensors could be placed within a patient's breast and surrounding anatomy and using wireless technology communicate with an embodiment of the radiotherapy system. The combination of implantable position sensors in communication with an embodiment of the radiotherapy system using one or more imaging modalities can accurately determine patient geometry in relation to the radiotherapy system geometry thereby allowing accurate and daily irradiation, or irradiation at a different schedule, of a patient concurrent with an individualized patient radiotherapy treatment plan.

Implantable or otherwise attachable dose monitoring sensors such as those available from Sicel Technologies, Inc. of Morrisville, N.C. can be used within an embodiment of the disclosed radiotherapy system in addition to or optionally independent of implantable position monitors. Implantable monitoring sensors such as those from Sicel Technologies, Inc. can collect and store data related for example to tumor cell kinetics and physiology, pH or oxygen levels, temperature, uptake and retention of chemotherapeutic agents, as well as the radiation dose delivered to a region of a patient's anatomy. Said monitoring sensors then use wireless technology to communicate collected data to receivers located outside a patient's body. In a preferred embodiment of the radiotherapy system, one or more implantable monitors can be used in a non-limiting example as radiation dose monitors and can be implanted in a patient at or near the lesion to be treated with therapeutic radiation and optionally surrounding tissue as well. Implanted radiation dose monitors are able to communicate to the radiotherapy system precisely what radiation dose is striking a patient's anatomy. Precise internal radiation dose information from implanted dose monitors can accurately provide dose information to doctors, physicians, and embodiments of the radiotherapy system herein thereby limiting over- or under-irradiation of a patient's anatomy and aiding in accurate and consistent daily treatment according to a patient's radiotherapy treatment plan. Stray radiation possibly striking other areas of a patient not intended to be irradiated can be monitored by properly implanted or otherwise secured dose monitors thereby increasing patient safety. Both position and dose monitors described herein are small devices capable of implantation using commercially available biopsy systems such as from the Suras Corporation, a subsidiary of the assignee of this patent specification, and methods in current clinical use.

FIG. 3 further illustrates degrees of freedom of the motion of patient table 101. The four directional arrows 302 represent the direction of motions along which motorized stand 106 can move prone table 101 (in addition to any up-down or tilting motion). In a preferred but non-limiting embodiment, table 101 can move approximately 10 centimeters in any direction from a resting position in the horizontal xy-plane parallel the floor. In a particular implementation, movement over distances greater or smaller than 10 cm can be selected. X and Y directions are shown by axis 305. Stand 106 also can be configured to move the patient table in the vertical position, and/or to tilt table 101, if desired. LINAC source 105 is shown in FIG. 3 at a 180° position relative to table 101. Arc 306 is placed in FIG. 3 for illustrative purposes to exemplify a curved direction of motion of LINAC source 105 around table 101, preferably about an isocenter of the system (not shown). In a non-limiting example, the rotational movement of LINAC source 105 can be combined with the vertical and horizontal movement of prone table 101 by motorized stand 106 allowing desired target volumes of a patient's breast and surrounding tissue to be imaged and receive appropriate doses of therapeutic radiation in accordance with an individual patient's radiation therapy plan.

Figure 4A:
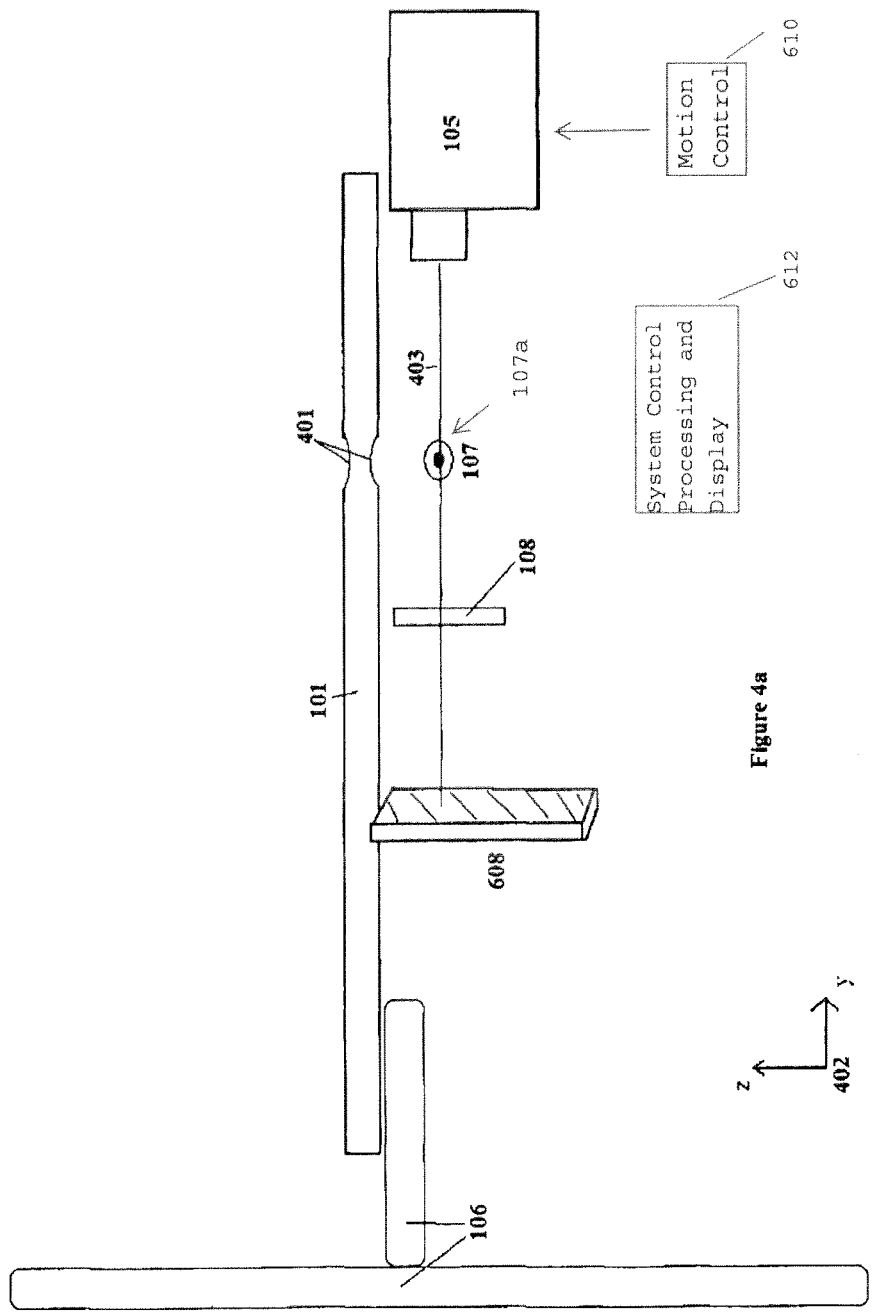
FIG. 4a illustrates a side view of a patient table and a center of rotation of the radiation source about an upwardly extending axis.

FIG. 4a is a side view of an example of the system, with LINAC source 105 at a 180° position around center 107. A radiation beam centerline 403 is shown of a shaped beam, e.g. a conical beam or a beam with a different cross-section and intensity distribution within the cross-section, exiting LINAC source 105, passing through center 107 and impinging on imaging detector 108. An additional feature is an optional beam blocker 608 that substantially stops primary photon energy that passes through imaging detector 108. Table 101, which is not shown to scale in terms of thickness, further comprises rounded openings 401 for a patient's breast, directly above center 107. Z-Y directional axis 402 is illustrated to show both the z-direction and y-direction of the system relative to the side view illustrated in FIG. 4a. A motion control 610 supports source 105, imaging detector 108, and beam blocker 608 and provides interface electrical and electronic connections between source 105, detector 108, and a sub-system 612 that serves as a system control and for processing and displaying data. Unit 610 and its connections to other units are shown schematically but it should be understood that the unit typically contains motors and associated components that impart the desired motions to source 105, imaging detector 108, and beam blocker 608, including motion in the horizontal plane (flat or curved) about center 107, tilting so that the motion about center 107 is in a plane (flat or curved) angled to the horizontal and such that at least source 105 can be at the level of or above patient table 101, and translating motion that moves center 107 to the left or to the right or up or down as seen in FIG. 4a. The schematic connections shown between unit 610 and source 105 and imaging detector 108 represent both mechanical and electrical/electronic two-way communication. The two-directional arrows in the connections to units 105, 108, and 608 schematically illustrate telescoping mechanism that can be motor-driven, e.g., by fluidic or electrical motors, up and down along the lengths of the mechanical supports. Unit 612 need not be under table 101; in fact, typically it is not in the same room as the therapy/imaging system. For clarity, the imaging systems illustrated in FIG. 1 are not shown in FIG. 4a but it should be understood that they can be mounted to and electrically/electronically connected to unit 610 in a manner in which their positions are known relative to the system frame of reference. Alternatively, they can be mounted and otherwise connected to a separate motion control and interface configured to move them in a way that does not interfere with the therapy radiation and portal imaging components. One of the motions of source 105 under patient table 101 about the patient's breast typically is in a horizontal plane; however, provisions can be and preferable are made for deviations from a motion in a flat plane, such as for motion in which the vertical elevation of source 105 varies during its motion about the breast. In addition, as discussed in greater detail below and shown by arrows in FIGS. 6a and 6b, source 105 can move to positions at the level of, or above, patient table 101.

Figure 4B:
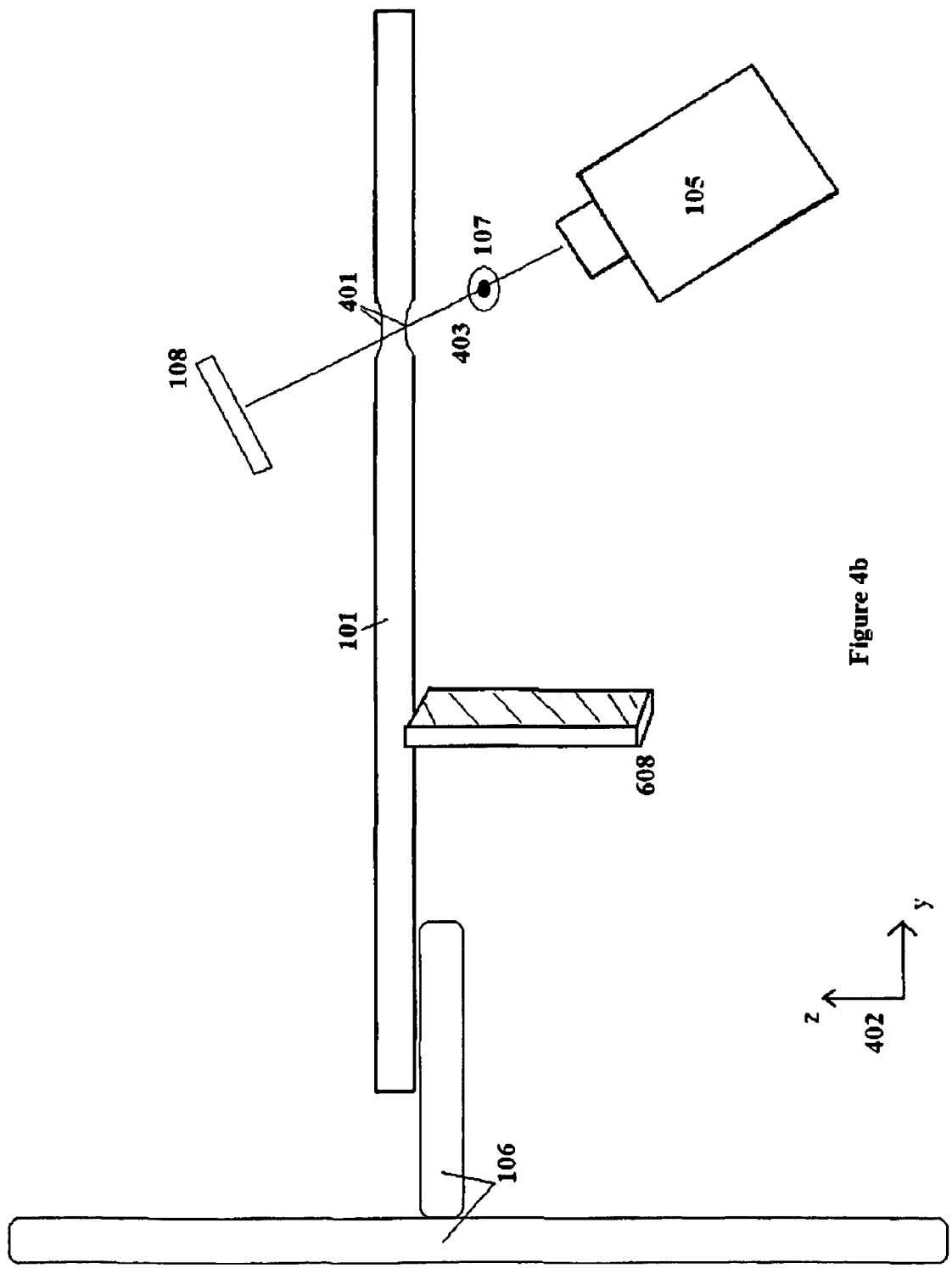
FIG. 4b illustrates a side view of a patient table and a center of rotation of the radiation source about a laterally extending axis.

FIG. 4b is similar to FIG. 4a but illustrates an additional capability of a preferred embodiment of the disclosed radiotherapy system. For clarity, units 610 and 612 and the mechanical and electrical/electronic connections of FIG. 4a are not shown in FIG. 4b but it should be understood that they are a part of the system as it would be seen in this configuration as well. During radiotherapy treatment of a breast or related anatomy, it is occasionally desirable to irradiate lymphatic systems and anatomical tissue located outside of the breast tissue hanging pendulant through an opening or into a depression in table 101. In these cases, an example being when breast cancer metastasizes, it is desirable to image and irradiate the lymphatic systems associated with a breast including axillary, parasternal, and pectoral nodes located in or near a patient's armpit area, collarbone area, or axillae. In these circumstances, the disclosed imaging and therapy system can optionally tilt radiation source 105 such that a centerline of a therapy radiation it emits is at an angle to the horizontal, e.g. at 45°-55°. As illustrated in FIG. 4b (where the angle is greater for clarity of illustration), an emitted radiation beam centerline 403 can pass upwards through a patient's armpit area and therapeutically irradiate lymphatic tissue and surrounding anatomical structures as desired. For this purpose, source 105 is mounted for movement about center 107 about a non-vertical axis, in a non-horizontal plane that can be flat or curved, and one or both of source 105 and detector 108 can be mounted for movement toward and away from center 107, along radiation centerline 403, and thus toward or away from a target volume Radiation detector 108 can be moved into a position above patient table 101, to remain perpendicular to the radiation beam centerline 403. In this case it is not necessary for the radiation beam centerline 403 to pass through an isocenter of the system. The precise pathway of the therapeutic radiation emitted from LINAC device 105 is determined by the treatment plan for a particular patient. Although not shown in FIG. 4b, optional beam blocker 608 also can be moved from below prone table 101 and positioned behind radiation detector 108 to absorb primary radiation still passing through detector 108.

Figure 5A:
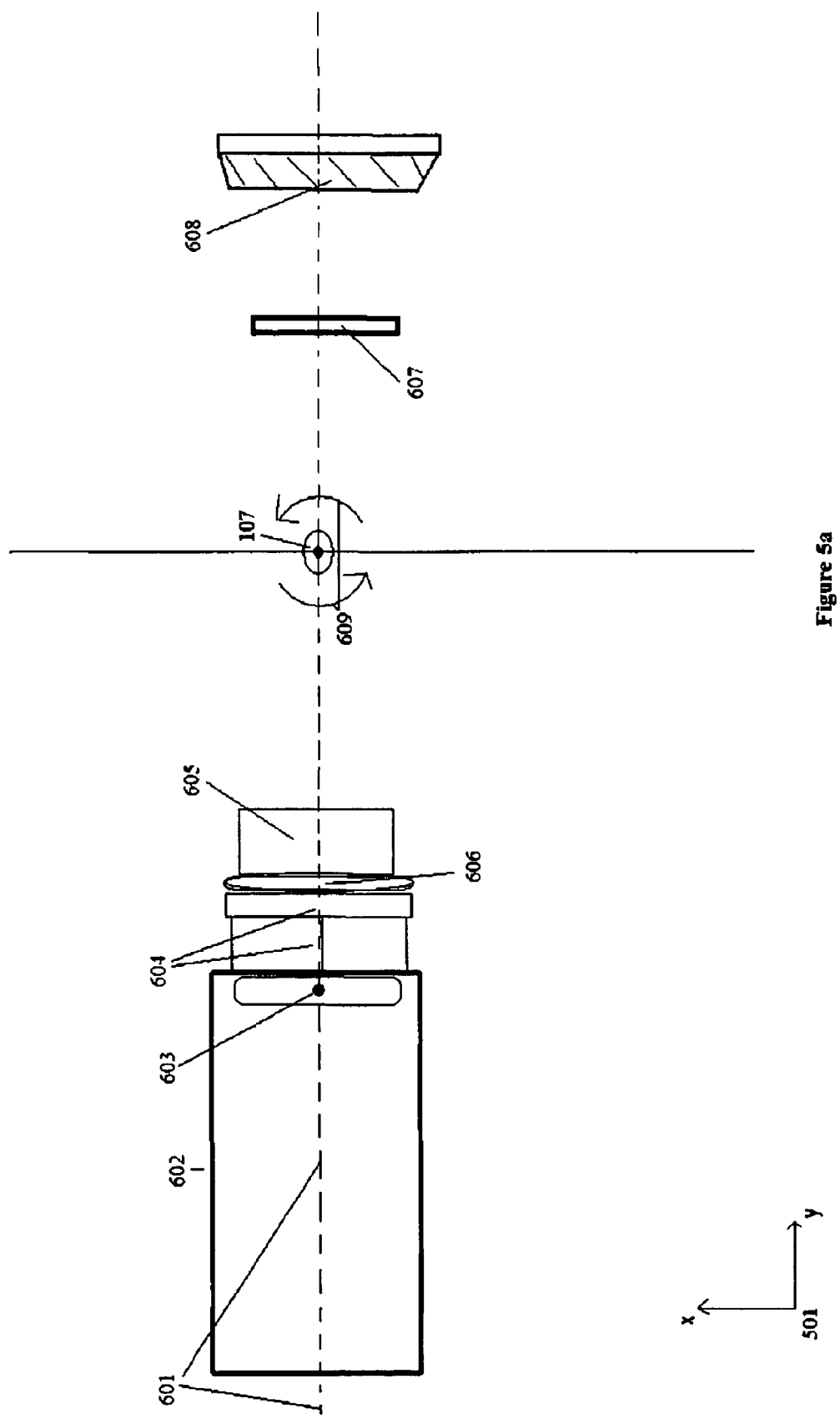
FIG. 5a illustrates a perspective view of the imaging/therapy system in relation to a desired isocenter of rotation.

FIG. 5a illustrates a top view of a portion of the radiotherapy system comprising an abstract depiction of a preferred center 107, a LINAC device 602 additionally a solid state flat panel detector 607, and an optional beam blocker 608. In the view of FIG. 5a the patient table normally located above the radiotherapy system as well as other components that are visible in other Figs. have been removed from the visual field so as to more easily illustrate features of a preferred embodiment of the radiotherapy system.

The radiotherapy system of FIG. 5a comprises a radiation beam centerline 601, a compact LINAC 602, a target assembly and carousel 603, a primary dual independent collimator 604, a tertiary multi leaf collimator 605, a monitor chamber for beam streams 606, a solid state panel detector 607 and optionally a beam blocker 608. Also shown in FIG. 5a is center 107 of the system, arrows 609 representing the direction of rotation of the LINAC in tandem with detector 607 and beam blocker 608, and x-y system 501 indicating the x-direction and y-direction of the machine in this illustration.

Figure 5B:
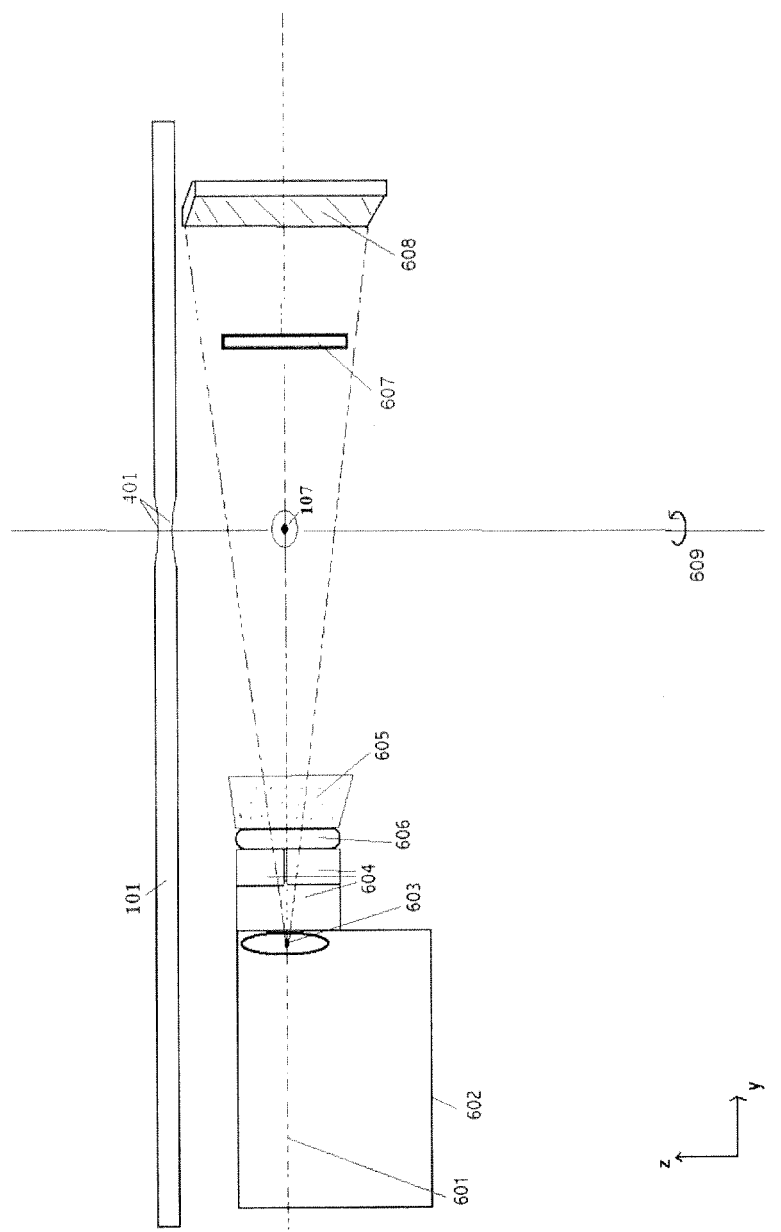
FIG. 5b illustrates a side view of the system.

FIG. 5b illustrates a side view of a preferred embodiment of a portion of the radiotherapy and imaging device used in the system shown in FIG. 5a. Again, for ease of illustration some components of the system that are visible in other Figs. have been omitted. As seen in FIG. 5b, the preferred embodiment comprises a linear accelerator (LINAC) 602, a target assembly and carousel 603, a primary collimator 604, a tertiary collimator 605, monitor chamber 606, a flat panel detector 607, and an optional beam blocker 608.

Figure 8:
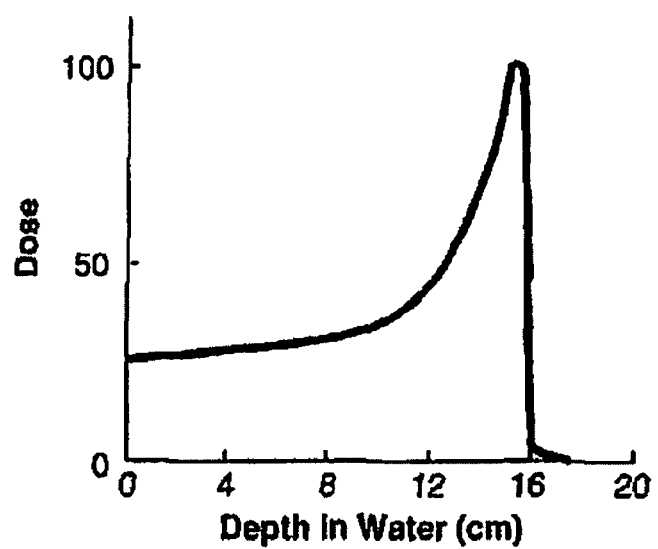
FIG. 8 illustrates depth dose distribution characteristic of heavy charged particles, with a Bragg peak.
Figure 9:
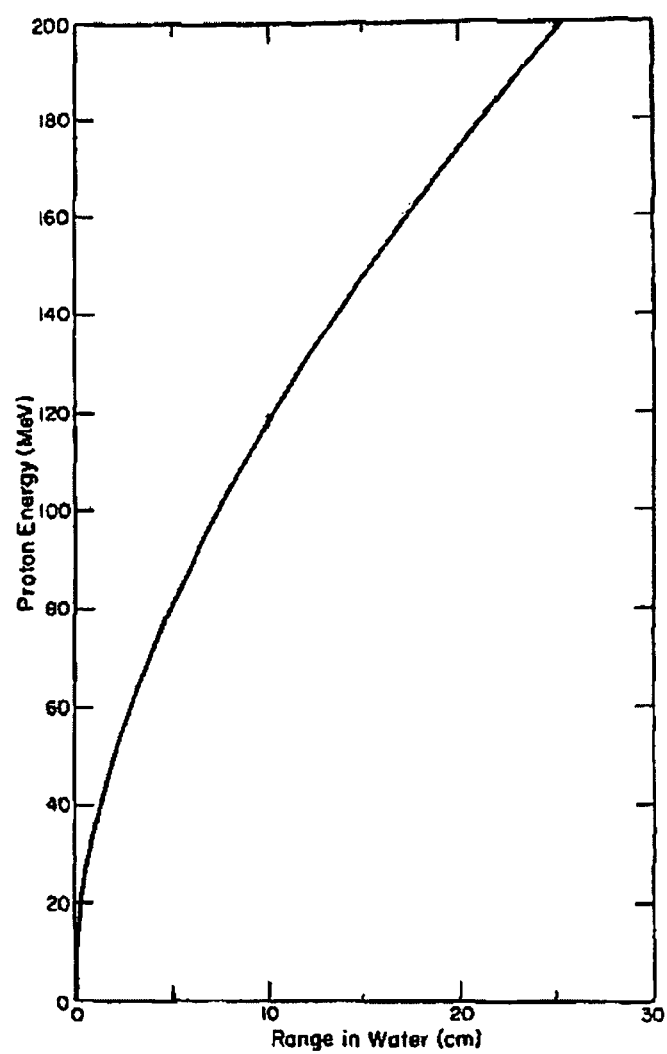
FIG. 9 illustrates range energy relationship for protons.

The radiation source 602 (which can but need not be a Linac source) in this embodiment preferably operates to produce one or more of the following four therapeutic forms of radiation: (i) direct electron (e−) beams, (ii) direct proton (p+) beams, (iii) high energy Bremstrahlung photons from an accelerator source, and (iv) high energy photons from a radioisotope (Cobalt-60). When high energy photons from a Bremstrahlung source are chosen as the therapeutic form of radiation then source 602 preferably operates to produce a stream of therapeutic photons having a maximum Bremstrahlung energy at or in the range 1 MeV to 10 MeV, preferably an average energy in the 4 MeV-6 MeV range, or in the 1 MeV-4 MeV range. In the most preferred configuration, a compact LINAC in the radiotherapy system produces a stream of therapeutic photons for irradiating breast tissue having an average energy in a specified range suitable for breast-related irradiation such as within the range of 1-2 MeV. As understood by applicants, a compact LINAC capable of producing therapeutic photons from a Bremstrahlung source wherein said photons have an average energy between 1-2 MeV, uses electrons with a peak energy preferably in the range of 1-6 MeV and more preferably within the energy range 4-6 MeV. Historically, as understood by applicants, LINAC manufacturers would have attempted to reproduce the effective energy of Cobalt 60 decay photons (1.25 MeV) when making LINAC sources for treating breast tissue. Cobalt-60 itself could also be used in the radiotherapy device claimed herein and the need for an accelerator removed. When a direct electron beam is selected as the therapeutic form of radiation, the LINAC preferably produces a stream of electrons, wherein the electrons have an energy range from 1-10 MeV, preferably in the range of 4-6 MeV When a direct beam of protons or other heavy charged particles (i.e., heavier than electrons) is used as the therapeutic form of radiation from a source such as 602, the energy range preferably is selected according to criteria such as discussed in "The Physics of Radiation Therapy", 3rd Edition, by Faiz Khan. Lippincott, Williams and Wilkins, ISBN 0-7817-3065-1, at pp. 56 & 57 (the "Book"). As seen in FIG. 8, which is a reproduction of FIG. 4.16 in the Book, for such heavy particles the characteristic distribution of radiation dose with depth in the irradiated tissue is different from that for photons and electrons. As the beam of heavy particles traverses tissue, the deposited dose is approximately constant with depth, or rises a little, until near the end of the depth range, where the dose peaks out to a high value followed by a rapid fall-off. The energy of other heavy charged particles, such as deuterons, stripped carbon atoms, and others, can be expressed in MeV/u, where u is the mass number of the nucleus, so that particles that have about the same MeV/u would be expected to have about the same range in water or tissue. According to the Book, for water the rapid rise starts at about 12 cm penetration depth, and peaks at about 15-16 cm and then rapidly falls off. As seen in FIG. 9, which is a reproduction of FIG. 4.17 in the Book, for 10-20 cm of water (to which breast tissue is similar in this respect), the proton energy range is approximately 80-180 MeV. Preferably, the average energy of the heavy charged particles from a source such as 602 exceeds 20 MeV, more preferably it exceeds 50 MeV, and most preferably it is in the range 80-180 MeV, in each case with a characteristic distribution with depth in breast tissue that has a Bragg peak followed by a rapid fall-off.

When a beam of heavy charges particles is used, an appropriate energy can be chosen to deposit the peak dose at the target volume of tissue. This can be particularly advantageous in the case of target volume that is at or close to the chest wall, because the rapid fall-off in dose after the peak leaves organs such as the lungs and heart with essentially zero dose. Another approach is to select heavy charged particles energy is to use energy corresponding to the average depth in the middle of the largest expected uncompressed breast.

Any of the forms of LINACs that are available from manufacturers such as Varian may also be made more compact and thus the machine size smaller by the utilization of superconductive wave guide materials and associated technologies such as currently being used to generate superconducting cyclotrons for treating other deep-seated lesions such as prostate cancer.

The radiation source 602 produces a radiation beam centerline that ideally passes from the exit of the source straight through a center of the system, which is usually the lesion of the breast being treated or is some line through another volume that should be subjected to radiation therapy.

The target assembly and carousel 603 included in the radiotherapy apparatus is used in an embodiment of the radiotherapy apparatus to switch the type of therapeutic radiation chosen for a particular volume in a patient's breast or surrounding tissue. In an electron mode, the radiotherapy apparatus can emit beta rays that are produced in a LINAC or comparable radiation source. While in a photon mode, the radiotherapy apparatus can be configured for the production of photons such as gamma or x-rays.

Following the target assembly and carousel is the primary dual independent collimator 604. The primary collimator 604 is followed by the tertiary or multi leaf collimator 605 that can produce in a non-limiting example a 3 mm leaf width at radiation and rotational center 107 of the system for precision treatment of voxels located within the breast.

The radiotherapy apparatus additionally can house a monitor chamber 606 positioned before the multi leaf collimator to assist in determining the amount of radiation being emitted from the radiation source and subsequently delivered to a particular volume in a patient. Preferably, monitor chamber 606 would remain in dynamic communication with a concurrent radiation monitoring system so that the radiotherapy system as accurately as possible provides therapeutic radiation in accordance with an individualized radiotherapy patient treatment plan.

After passing through the center 107, the radiation strikes a solid state flat panel detector 607 used for portal imaging. The flat panel detector 607 is moveable relative to the beam of radiation so that it can be placed in the path of the beam for imaging and taken out of the path of the beam for radiation treatment.

Optionally, a beam blocker 608 can be placed in the path of the beam to effectively stop radiation that has passed through the irradiated volume. As shown in FIGS. 5a and 5b, optional beam blocker 608 is placed within the path of the radiation emitted from source 602 illustrated by photon beam centerline 601 and positioned downstream of center 107 and flat panel detector 607. The optional beam blocker 608 can cut down the cost of shielding the room thereby reducing the structural footprint of a room housing this system, and making the system as a whole easier and less expensive to install and operate in hospitals, clinics, and other such facilities.

FIGS. 6a and 6b illustrate a variation of the system in which patient table 101 is supported on a motorized pedestal 650 that can selectively move table 101 along some or all the x, y, and z axes illustrated in FIGS. 6a and 6b, and also can tilt table 101 about some or all of these the axes. Another motorized pedestal 652 supports a motorized plate 654 that in turn supports an arm 656 to which is mounted another arm 660 supporting therapy radiation source 105, portal imaging detector 108, and blocking plate 608 and any imaging system schematically illustrated at 658. Pedestal 652 selectively rotates plate 654 to move arm 656 and the components it carries between the positions shown in solid and in dotted lines, including any intermediate position. Motorized plate 654 selectively moves arm 656 and the components attached to it up and down as illustrated by arrows in the z-direction and also telescopes or otherwise extends arm 656 and the components it carries in the y-direction as also illustrated by a bidirectional arrow. Arm 656 also can be motorized to selectively rotate arm 660 about the z-axis at point 662 as illustrated by a bidirectional curved arrow. In addition, arm 660 can be motorized to selectively rotate radiation source 105 about the x-axis at 664 as illustrated by another bidirectional curved arrow. These translational and rotations motions are powered and controlled by units such as 610 and 612 (FIG. 4a) that are omitted from the illustration in FIGS. 6a and 6b for clarity. FIG. 6b illustrates the same arrangement as FIG. 6a but in a front elevation. Typically the patient would be prone on table 101, with a breast extending downwardly through an opening or into a depression in table 101, so that the breast and/or related tissue can be imaged and/or treated with radiation from below table 101, through the motions referred to above patient tissue can also be treated with a radiation beam that extends from below table 101 through the patient at an angle to the horizontal, for example as illustrated in FIG. 4b, or at any other suitable angle to the horizontal. Alternatively, if desired the patient can be in another position, such as the supine position, to be imaged and/or treated with radiation from a source position above table 101, such as illustrated in dotted lines in FIGS. 6a and 6b.

FIG. 7 illustrates in side elevation an alternative that includes, in addition to the arrangement of FIGS. 6a and 6b, an arm 700 that is at the other side of patient table 101 and is mounted to plate 654 in a manner similar to that used for arm 656. Again, plate 654 can be motorized to selectively move arm 700 up and down as seen in FIG. 7 and illustrated by arrows, and to extend or contract arm 700 in the y-direction as illustrated with a bidirectional arrow. Arm 700 carries a specialized breast CT scanner 712 that is otherwise similar to commercially available CT scanners available from companies such as Giotto of Italy and distributed in this country primarily for imaging extremities by Hologic, Inc. of Bedford, Mass. but is smaller and lighter to serve as a dedicated breast CT scanner. Other breast-specific CT scanners are proposed by Dr. John Boone (see Synthesis, a publication of UC Davis Cancer Center, Vol. 8, No. 2, Fall/Winter 2006) and by Koning Corporation of West Henrietta, N.Y., and can be adapted for mounting in the system disclosed in this patent specification. When plate 654 rotates about the y-axis such that arm 700 is below patient table 101, a patient breast extending downwardly from the upper surface of table 101 can be positioned in an opening 714 of CT scanner 712 and conventional CT scanning can be carried out to generate or adjust or verify treatment plans for treatment that can be carried out with the equipment mounted to arm 656. The components and motions in FIG. 7 that are in addition to those associated with arm 700, including ones not labeled or otherwise marked in FIG. 7, can be the same as in FIGS. 6a and 6b.

The imaging functionalities of the disclosed system and method can be used to assist in brachytherapy; for example to verify the placement of radiation sources in the breast relative to breast anatomy, and to monitor the treatment. Some of the challenges of brachytherapy are to ensure that the distance along different directions between the radiation source inside the breast and the surrounding tissue conforms to the treatment plan, and that the tissue to be treated is the planned tissue. Before the radiation source is introduced or turned on, images may be taken with a modality such as a CT scanner to confirm that the source is positioned well and to account to anatomy issues such as seromas, scar tissue, and hematomas. If a whole-body CT scanner is used, as is common, the imaging radiation traverses not only the breast that is being treated but also the other breast and the thorax. After a treatment session, more verification images may be taken. Using the imaging and treatment planning facilities of the system and method described here would involve imaging radiation dose delivered only to the breast being treated, and also would facilitate obtaining good images in the prone position, with the patient's breast extending down.

Various types of brachytherapy instruments can be used, such as those offered by the assignee of this patent specification under the name Mammosite, by North American Scientific of Chatsworth, Calif., by Cianna Medical of California (formerly Biolucent), by SenoRx of Aliso Viejo, Calif., and other companies. Verification of brachytherapy treatment parameters using the imaging equipment described in this patent specification can be done before, during and/or after brachytherapy treatment and can involve placing the patient one or more times in the prone position on a patient table surface such as 101 in FIG. 7, with the patient's breast pendulously extending downwardly in an opening or depression in the table surface, and imaging the breast using any one or more of the modalities discussed in connection with FIG. 7, to obtain 2D and/or 3D images of the breast and use the resulting image data for one or more of the following processes: (1) assessing suitability of the breast for brachytherapy; (2) brachytherapy planning, including what brachytherapy device to use, in what way, what radiation agent to use and in what way, the treatment plan in terms of fractional and total dose, and other parameters related to brachytherapy treatment of the breast; (3) verifying and if needed adjusting the placement of brachytherapy devices in the breast or changing brachytherapy devices and/or internal radiation sources as desired, for example to ensure good contact between the device and breast tissue in the surgical cavity and to consider and account for anatomical features such as seromas and other anatomical irregularities; (4) assessing effects of brachytherapy treatment such as changes in breast tissue at or near the surgical cavity, and possibly modifying the treatment plan as a result of such assessment; and (5) post brachytherapy assessments. One significant benefit of using for this purpose the system described in this patent specification is that only an affected breast is being imaged so that if penetrating radiation is used, no primary beam will be directed to other tissue. Another is that because the disclosed system can use a variety of imaging modalities, the health professional can select one or more modalities best suited for the patient. Still another benefit is that brachytherapy of a breast can be combined with treatment radiation of the same breast or of related tissue in the same system, from an external source of radiation, while the patient is in the same position on the same patient table surface used for imaging, such as the system of FIG. 7.

All patents and other publications and patent application identified above are hereby incorporated by reference in this patent specification.

While specific example of various features of the disclosed inventions are discussed above, it should be clear that they are not intended to be the only examples of the inventions described in the claims below, and should not be construed as limitations on the scope of the claimed inventions, which scope includes many additional and alternative examples and variation that would be appreciated by persons skilled in the art as being equivalent or as being otherwise within the scope of the claimed inventions.

The invention claimed is:

1. A method of verifying brachytherapy treatment comprising:
    inserting one or more brachytherapy devices into a breast of a patient;
    after insertion of the one or more brachytherapy devices into the patient breast, placing the patient in a prone position on a patient table surface having an opening or depression in which the patient's breast for brachytherapy treatment extends downwardly, wherein one or more brachytherapy devices remain located inside the breast during placement into the prone position;
    CT imaging the breast with radiation to verify brachytherapy related parameters using an imaging device located below the patient table surface, while the one or more brachytherapy devices remain located inside the breast during CT imaging;
    said brachytherapy related parameters including a position of the one or more brachytherapy devices that have remained located inside the patient's breast relative to anatomy of the breast; and
    generating image data for the patent's breast for assessing brachytherpay-related parameters, including image data related to said position of said one or more brachytherapy devices that have remained located inside the breast relative to breast tissue adjacent to said one or more brachytherapy devices.

2. The method of claim 1, in which the CT imaging comprises using an imaging x-ray beam having a centerline that is below the patient table surface on which the patient is placed.

3. The method of claim 1, in which the CT imaging comprises detecting radiation emitted from the one or more brachytherapy devices.

4. The method of claim 1, in which the image data include parameters related to effects of treatment by the one or more brachytherapy devices on adjacent tissue.

\* \* \* \* \*